United States Patent
Wijshoff et al.

(10) Patent No.: US 11,406,562 B2
(45) Date of Patent: Aug. 9, 2022

(54) DEVICE, SYSTEM, AND METHOD TO CONTROL ACTIVATION AND CONFIGURATION OF PULSE DETECTION AND PULSE OXIMETRY MEASUREMENTS DURING CPR

(71) Applicant: KONINKLIJKE PHILIPS N.V., Eindhoven (NL)

(72) Inventors: Ralph Wilhelm Christianus Gemma Rosa Wijshoff, Munstergeleen (NL); Jakob Van De Laar, Oosterhout (NL); Jens Muehlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/270,875

(22) PCT Filed: Jul. 7, 2020

(86) PCT No.: PCT/EP2020/069044
§ 371 (c)(1),
(2) Date: Feb. 24, 2021

(87) PCT Pub. No.: WO2021/008925
PCT Pub. Date: Jan. 21, 2021

(65) Prior Publication Data
US 2022/0142858 A1    May 12, 2022

(30) Foreign Application Priority Data

Jul. 18, 2019  (EP) .................................. 19186879

(51) Int. Cl.
*A61H 31/00*    (2006.01)
*A61B 5/024*    (2006.01)
(Continued)

(52) U.S. Cl.
CPC ....... *A61H 31/005* (2013.01); *A61B 5/02416* (2013.01); *A61B 5/14551* (2013.01);
(Continued)

(58) Field of Classification Search
CPC ... A61H 31/004; A61H 31/005; G09B 23/288
See application file for complete search history.

(56) References Cited

U.S. PATENT DOCUMENTS

| 8,744,542 B2 | 6/2014 | Ukawa | |
|---|---|---|---|
| 2006/0224073 A1* | 10/2006 | Lin | A61B 5/6826 600/513 |

(Continued)

FOREIGN PATENT DOCUMENTS

| JP | 2016198656 A | 12/2016 |
|---|---|---|
| KR | 20180031991 | 3/2018 |

(Continued)

OTHER PUBLICATIONS

PCT/EP2020/069044 ISR & WO.
(Continued)

*Primary Examiner* — Samchuan C Yao
*Assistant Examiner* — Nathan M Le

(57) ABSTRACT

A device, system, and method to control activation of oxygen saturation (SpO2) measurements in a cardio-pulmonary resuscitation (CPR) procedure. When compressions are present, only a PPG-based pulse detection algorithm is performed. When a spontaneous pulse has been detected and compressions are not detected during a predetermined time period, both a PPG-based pulse detection algorithm and an SpO2 measurement algorithm are performed. Depending on whether a chest compression is delivered manually or automatically, parameter selections for the compression detec-
(Continued)

Automatic activation and deactivation of the SpO2 measurement tion algorithm, the PPG-based pulse detection algorithm, and the SpO2 measurement algorithm are adjusted accordingly.

15 Claims, 6 Drawing Sheets

(51) Int. Cl.
 *A61B 5/1455* (2006.01)
 *A61B 5/00* (2006.01)
(52) U.S. Cl.
 CPC .......... *A61B 5/748* (2013.01); *A61H 31/006* (2013.01); *A61H 31/007* (2013.01); *A61H 2201/5046* (2013.01); *A61H 2201/5058* (2013.01); *A61H 2201/5061* (2013.01); *A61H 2201/5071* (2013.01); *A61H 2201/5079* (2013.01); *A61H 2201/5084* (2013.01); *A61H 2230/201* (2013.01)

(56) References Cited

U.S. PATENT DOCUMENTS

| | | | | |
|---|---|---|---|---|
| 2012/0010543 | A1* | 1/2012 | Johnson | A61H 31/00 601/41 |
| 2012/0016279 | A1* | 1/2012 | Banville | A61B 5/318 601/41 |
| 2012/0245442 | A1* | 9/2012 | Ukawa | A61H 31/005 600/324 |
| 2015/0164339 | A1* | 6/2015 | Xu | A61B 5/7282 600/324 |
| 2018/0092804 | A1* | 4/2018 | Hunt | A61N 1/39044 |
| 2018/0185240 | A1* | 7/2018 | von Schenck | A61H 31/005 |
| 2018/0207058 | A1 | 7/2018 | Xu et al. | |
| 2018/0256043 | A1* | 9/2018 | Melker | A61H 31/006 |
| 2019/0231641 | A1 | 8/2019 | Banville | |

FOREIGN PATENT DOCUMENTS

| | | |
|---|---|---|
| WO | 2015121114 A1 | 8/2015 |
| WO | 2017072055 A1 | 5/2017 |
| WO | 2017211814 A1 | 12/2017 |
| WO | 2019201689 A1 | 10/2019 |

OTHER PUBLICATIONS

Link et al: "Part7: Adult Advanced Cardiovascular Life Support, 2015 American Heart Association Guidelines Update for Cardiopulmonary Resuscitaiton and Emergency Cardiovascular Care"; Circulation, 2015, pp. S444-S464.

Soar et al: "European Resuscitation Council Guidelines for Resuscitation 2015 Section 3. Adult Advanced Life Support"; Resuscitation 95, 2015, pp. 100-147.

Wijshoff et al: "Photoplethysmography-Based Algorithm for Detection of Cardiogenic Output During Cardiopulmonary Resuscitation": IEEE Transactions on Biomedical Engineering , vol. 62, No. 3, Mar. 2015, pp. 909-921.

Wijshoff et al: "Detection of a Spontaneous Pulse in Photoplethysmograms During Atuomated Cardiopulmonary Resuscitation in a Porcine Model"; Resuscitation 84, 2013, pp. 1625-1632.

* cited by examiner

DEVICE, SYSTEM, AND METHOD TO CONTROL ACTIVATION AND CONFIGURATION OF PULSE DETECTION AND PULSE OXIMETRY MEASUREMENTS DURING CPR

CROSS-REFERENCE TO PRIOR APPLICATIONS

This application is the U.S. National Phase application under 35 U.S.C. § 371 of International Application No. PCT/EP2020/069044, filed on Jul. 7, 2020, which claims the benefit of European Patent Application No. 19186879.3, filed on Jul. 18, 2019. These applications are hereby incorporated by reference herein.

FIELD OF THE INVENTION

The inventive subject matter relates to devices, systems and methods to control activation and configuration of pulse detection and pulse oximetry (SpO2) measurements during a cardiopulmonary resuscitation (CPR) procedure.

BACKGROUND OF THE INVENTION

CPR is an emergency procedure for people suffering from a cardiac arrest. During CPR, chest compressions are delivered to artificially generate circulation of blood, and ventilations are given to supply blood with oxygen. The goal of CPR is to achieve return of spontaneous circulation (ROSC). When ROSC has been achieved, the heart of the patient has resumed beating and generates a spontaneous circulation which is life-sustaining. CPR can be stopped after achieving ROSC.

Detecting ROSC during CPR is challenging and time consuming. Determining whether a patient has achieved ROSC involves checking whether the patient has a spontaneous circulatory pulse, i.e., whether the heart is beating and is generating output. Typically, ROSC detection involves manual palpation for an arterial pulse, which requires interrupting the chest compressions. CPR procedures generally benefit from improved monitoring and feedback during the procedure. For example, EP 2502560 A1 describes a CPR monitoring apparatus to obtain an oxygen saturation value during ongoing compressions in order to assess and improve the quality of the chest compressions. Additionally, after a spontaneous pulse has returned and chest compressions have stopped, clinicians want to know the patient's oxygen saturation to further monitor the patient and tailor the patient's treatment.

Hence, there is an ongoing need to improve the CPR work-flow aspects of pulse detection and SpO2 measurements in cardiac monitoring devices and to minimize disadvantages associated with interruptions of the chest compression sequence being performed on a patient.

SUMMARY OF THE INVENTION

The disclosed subject matter relates to usability aspects of the combination of pulse detection and SpO2 measurements throughout a CPR procedure.

Pulse detection during CPR can be performed by using photoplethysmography (PPG), for example as described in R. W. C. G. R. Wijshoff, et al: "Detection of a spontaneous pulse in photoplethysmograms during automated cardiopulmonary resuscitation in a porcine model," Resuscitation, vol. 84, no. 11, pp. 1625-32, November 2013, which is hereby incorporated by reference in its entirety, disclosing an investigation of the potential of PPG signals to detect the presence and rate of a spontaneous cardiac pulse during CPR, by retrospectively analyzing PPG and arterial blood pressure signals simultaneously recorded in pigs undergoing automated CPR.

The use of PPG signals to support detection of ROSC during CPR has been described, for example in WO2015121114 (A1) "Method and apparatus for minimizing detrimental interruptions in the chest compression sequence during cardiopulmonary resuscitation", which is hereby incorporated by reference in its entirety, and WO2017211814 "System and methods for photoplethysmography-based pulse detection support during interruptions in chest compressions", which is hereby incorporated by reference in its entirety.

Algorithms based on PPG signals to detect ROSC may be found, for example, R. W. C. G. R. Wijshoff, et al: "Photoplethysmography-Based Algorithm for Detection of Cardiogenic Output During Cardiopulmonary Resuscitation," IEEE Trans. Biomed. Eng., vol. 62, no. 3, pp. 909-921, 2015, which is hereby incorporated by reference in its entirety, describes a PPG-based algorithm that supports ROSC detection by combining the compression-free PPG signal with an indicator based on the detected perfusing rhythm and redistribution of blood volume. Further examples of algorithms used to analyze PPG signal content to support detection of ROSC may be found in US 2016/0157739 or WO 2017/072055.

According to the inventive subject matter, oxygen saturation measurements are activated in absence of chest compressions and when a spontaneous pulse has returned. Since the PPG signals for pulse rate (PR) and SpO2 measurements can be collected by the same pulse oximetry hardware and optimal settings of the pulse oximetry hardware differ for PR only measurements and for PR and SpO2 measurements, the settings of the pulse oximetry hardware are automatically adjusted to PR only measurement and to PR and SpO2 measurements, to provide optimal performance in each scenario. The SpO2 algorithm can be activated by a manual mode to switch on SpO2 measurement or by an automatic mode to switch on SpO2 measurements. Additionally, the pulse detection algorithm has different optimal settings for manual and automated chest compression delivery. The optimal settings for the pulse detection algorithm are automatically determined by the monitor-defibrillator device, for example by analysis of an impedance signal or another compression reference signal. Pulse oximetry hardware can perform this type of analysis during compressions, thereby minimizing interruptions to the chest compression sequence, and extend the analysis with an SpO2 measurement when compressions have stopped and a spontaneous pulse has returned.

One advantage of the inventive subject matter described herein is that it provides for convenient automatic activation of SpO2 measurements and convenient automatic optimal configuration of the pulse oximetry hardware and pulse detection algorithm, without specific user intervention other than normally performed clinically.

This Summary is not intended to limit the scope or meaning of the disclosed subject matter. Further, the Summary is not intended to identify key features or essential features of the disclosed subject matter, nor is it intended to be used as an aid in determining the scope of the disclosed subject matter.

DETAILED DESCRIPTION OF EMBODIMENTS

The disclosed subject matter will become better understood through review of the following detailed description in conjunction with the figures. The detailed description and figures provide example embodiments of the invention described herein. Those skilled in the art will understand that the disclosed examples may be varied, modified, and altered without departing from the scope of the invention described herein.

Throughout the following detailed description, various examples of devices, systems and methods to control activation and configuration of pulse detection and SpO2 measurements during the CPR procedure are provided. Related features in the examples may be identical, similar, or dissimilar in different examples. Related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature or example. Also, the drawings are not necessarily to scale, emphasis instead generally being placed upon illustrating the principles of the inventive subject matter.

The present disclosure focusses on the work-flow aspects of a CPR procedure, in particular on how to conveniently activate the pulse detection and SpO2 algorithms in CPR related devices while minimizing interruptions to the procedure. As such, the inventive subject matter allows for activation of the SpO2 measurement when it is required and reliable, i.e., the SpO2 measurement algorithm is deactivated when compressions are present, and the SpO2 measurement algorithm is activated when a spontaneous pulse has been detected and compressions are not detected during a predetermined time period. Additionally, the inventive subject matter allows automatic optimization of the pulse oximetry hardware settings depending on whether PR only or PR and SpO2 need to be measured, and automatic configuration of the pulse detection algorithm for optimal performance. In some embodiments, user intervention may be as standard in clinical practice such as changing device mode. In other embodiments, there is no user intervention at all.

Figure 1:
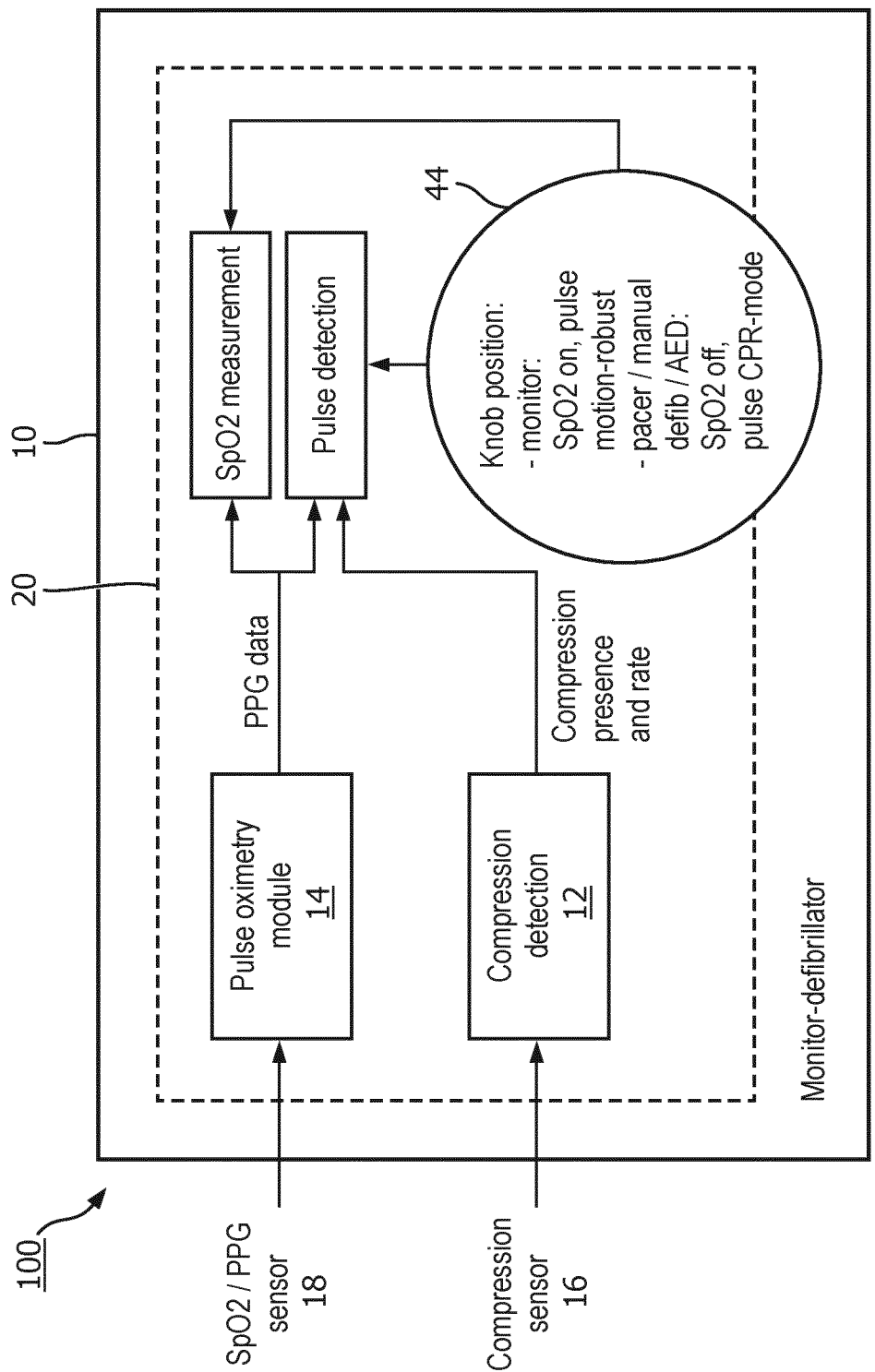
FIG. 1 is a schematic diagram of a first embodiment of a system including a manual mode to activate the SpO2 algorithm.

FIG. 1 illustrates a first embodiment wherein a system 100 and device 10 include a manual mode to activate the SpO2 algorithm. Device 10, for example a monitor-defibrillator or advanced automated external defibrillator (AED), includes a compression detection module 12 and a pulse oximetry module 14. Compression detection module 12 receives a compression signal from a compression sensor 16 and provides compression presence data and compression rate data. Pulse oximetry module 14 receives one or more PPG signals from an SpO2/PPG sensor 18 and provides PPG data. During a CPR procedure, device 10 runs the PPG-based pulse detection algorithm and the activation of the SpO2 measurement is linked to a mode selection of a user input switch 44.

The device 10 contains a signal processing unit 20 with access to or including one or more predetermined algorithms. Signal processing unit 20 receives PPG signals and compression signals via suitable input ports of device 10. In this embodiment, signal processing unit 20 is adapted to perform a pulse detection algorithm with the retrieved compression presence and rate data to determine whether a pulse is present. For example, compression detection module 12 is configured to determine a compression condition of "compression", "no compressions", or "artifact" from the signal input data as well as the compression rate when compressions are being delivered. Signal processing unit 20 is also adapted to perform a PPG-based pulse detection algorithm and an SpO2 measurement algorithm based on the received PPG data to provide pulse detection and SpO2 measurements. Here, the PPG-based pulsed detection algorithm may make use of the information provided by the compression detection, e.g., to distinguish between compression-related and spontaneous pulse related components in a PPG signal. In some embodiments, system 100 may include other physiological sensors and perform related algorithms in addition to the ones described herein.

As used herein, the term "signal processing unit" describes various apparatus relating to the operation of the medical device, system, and method. The processing unit can be implemented in numerous ways to perform the various functions described herein. For example, the signal processing unit can include a combination of dedicated hardware to perform some functions and a processor, such as one or more microprocessors that may be programmed using software to perform various functions discussed herein. "Signals", "inputs", and "outputs" may be understood to be electrical or optical energy impulses which represent a particular detection of processing result. In various implementations, the processing unit may be associated with one or more computer storage media, for example volatile and non-volatile computer memory, and may be fixed within a processor or controller or may be transportable.

Signal processing unit 20 is configured to analyze the chest compression signal to discriminate a pause in compressions from ongoing compressions. If the compression signal is determined to indicate a compression rate below a predefined threshold or is determined not to contain compression-related characteristics, signal processing unit 20 assesses that there are no chest compressions being delivered to the patient, i.e. that there is a pause in compressions. Identifying a pause in compressions based on the compression signal can be used to obtain an alternative detection of presence or absence of the spontaneous cardiac component and the spontaneous pulse rate in the PPG signal. If the compression signal is determined to indicate a compression rate within a specified range of compression rates, signal processing unit 20 assesses that there are chest compressions being delivered to the patient. In this case, the compression rate can also be provided by the compression detection 12 to the pulse detection and this information can be taken into account by the pulse detection to discriminate between compression components and spontaneous pulse components and identify the spontaneous pulse component and the spontaneous pulse rate. Signal processing unit 20 executes computer program instructions and algorithmic functions related to CPR compressions and processes the SpO2 signal and PPG signal, for example as described in WO2017/211814.

Figure 2:
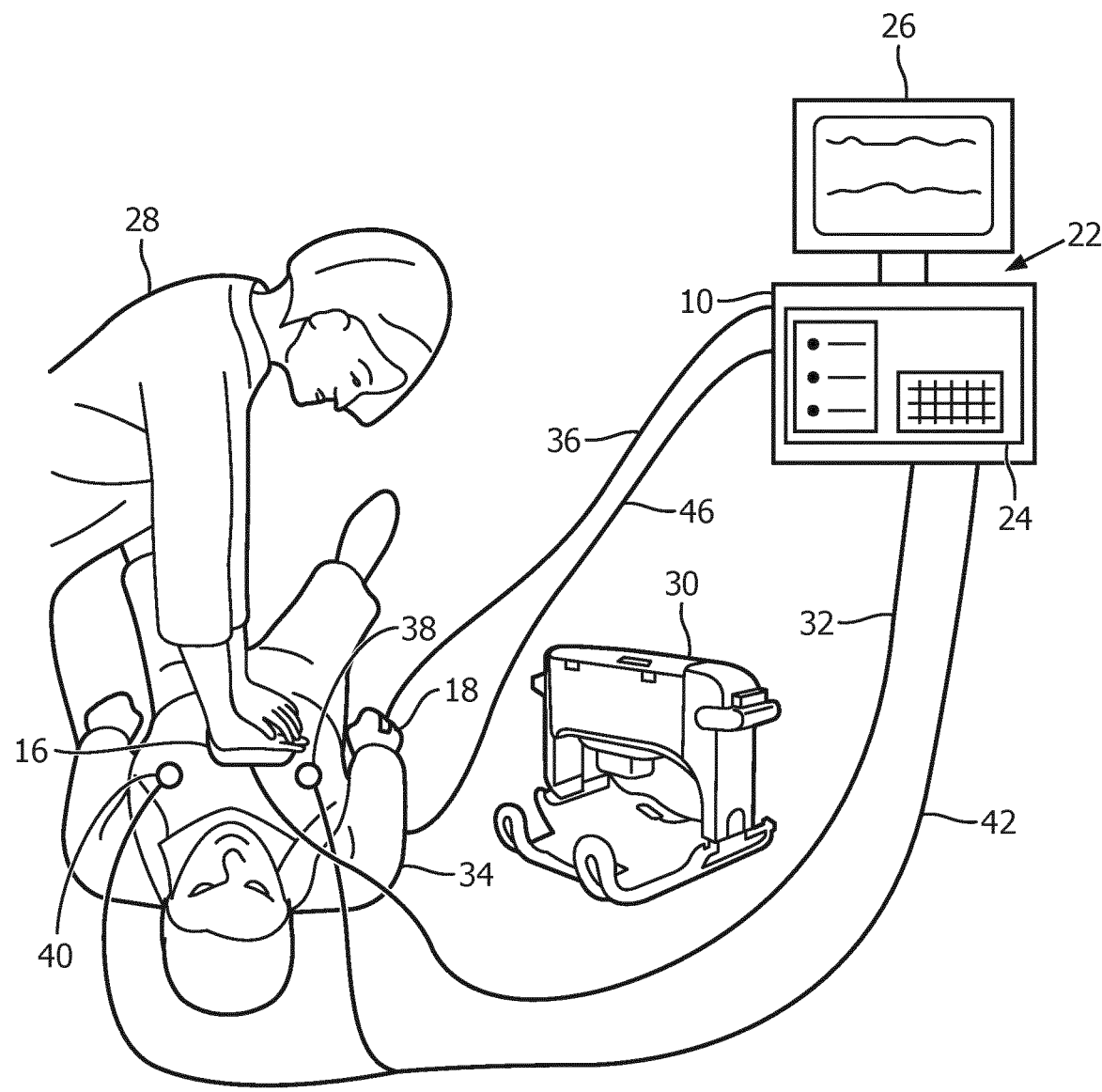
FIG. 2 shows an exemplary implementation of the system illustrated in FIG. 1.

FIG. 2 illustrates an exemplary implementation of system 100. The main goal of CPR is to achieve ROSC, in which situation the patient's heart has resumed beating. To determine whether ROSC has been achieved, pulse detection is typically performed throughout the CPR procedure. For example, device 10 can include pulse oximetry module 14 as illustrated in FIG. 1 and can be used for PPG-based pulse detection and SpO2 measurements. Pulse detection can be obtained by analyzing a PPG signal obtained from an SpO2/PPG sensor 18, for example arranged in a finger cuff. In other embodiments, the PPG measurement could be obtained using a PPG sensor applied to the forehead, the nasal septum, the alar wing, the earlobe, the concha of the ear, or any other suitable location on the patient.

Once the heart of the patient has resumed beating, clinically it is desirable to know the patient's SpO2 levels. PPG signals can be measured during CPR using standard SpO2 sensors and hardware. For example, SpO2 can be determined from a red and an infrared PPG signal, as measured with a standard SpO2 sensor. Thus, allowing a single SpO2 probe to be used for both pulse detection and SpO2 measurements. However, during cardiac arrest SpO2 measurements are not feasible, and during chest compressions SpO2 measurements are not reliable. Basic hemodynamic features may disappear with a cardiac arrest, in which case the sampled signal may look like a noise line. Therefore, only when there is pulse present and there are no compressions, the SpO2 algorithm should be activated.

Output of signal processing unit 20 can be displayed on a user interface 22 having one or more displays, buttons, touchscreens, keyboards or other human machine interface means. In the illustrated example, a first user interface 24 and a second user interface 26 function as a patient monitor. The first and second user interface may consist of separate units formed as a single unit, for example a single user interface configured to obtain user information and to provide ROSC information.

Compression detection module 12 detects a signal of a timing of a chest compression during a CPR procedure. The signal may be obtained from a compression sensor 16, for example a displacement sensor, a speed sensor, an acceleration sensor, a force sensor or a pressure sensor or other suitable compression signal sensor attached to the patient's chest and subject to compression. Compression detection module 12 can be based on pad impedance, compression depth, compression velocity, compression acceleration or compression force. In some embodiments, an accelerometer can provide information regarding CPR compression frequency, phase, and acceleration, velocity and depth as well as compression pauses. A PPG signal can be measured during a pause in compressions, wherein the pause in chest compressions can be detected with a compression signal being delivered via a chest compression cable 32 from the chest compression sensor 16 to device 10. Chest compressions can be delivered either manually by a clinician 28, for example, or with an automated mechanical device 30.

The system 100 may include other physiological sensors, such as a blood pressure sensor 34 arranged in an inflatable arm cuff and coupled to device 10 via cable 46, and ECG sensors 38, 40 attached to the patient's chest and both coupled to device 10 via cable 42. The device can also be connected to a set of defibrillator pads. This allows the algorithm to know when the shock is given and to obtain information on the chest compressions, for example with a transthoracic impedance measurement.

The PPG signal can be delivered via a PPG cable 36 from SpO2/PPG sensor 18 in the finger cuff to device 10 and is analyzed by a signal processing unit of device 10 for presence of a spontaneous pulse. To support such analysis ECG signals measured by the ECG sensors 38, 40, and provided to the device 10 via an ECG cable 42, may be used. Furthermore, system 100 may also measure and analyze PPG signals for pulse presence during ongoing compressions. A blood pressure measurement can be performed during a pause in compressions, either automatically or after a confirmation from the user via user interface 24. If compressions are delivered in cycles of two minutes, for instance, as is customary in CPR, a blood pressure measurement can be scheduled for the short pause directly following the two-minute cycle of compressions. Alternatively, the system can prompt to the clinician 28 that a spontaneous pulse has been detected and suggest starting the blood pressure measurement directly after pressing a button of the first user interface 24. In the latter case the clinician 28 has the option not to wait for the next pause in the protocol but deviate from the standard protocol to personalize the treatment to a patient.

In this first embodiment, activation of the SpO2 measurement algorithm is linked to a mode-selection of device 10. Here, device 10 has four operating modes: monitor mode, pacer mode, manual defib mode and AED mode. The basic assumption is that pacer/manual defib mode/AED mode are used during CPR and that the device is switched to monitor-mode once ROSC has been achieved.

If device 10 is in pacer/manual defib/AED mode, only the PPG-based CPR pulse-detection algorithm is activated. The pulse detection algorithm can indicate pulse presence only or can provide the PR in addition.

If device 10 is in monitor mode, the pulse detection algorithm and the SpO2 algorithm are both activated. The SpO2 measurement can, for example, be activated only in monitor-mode and not in pacer/manual defib/AED mode. In the monitor mode, the pulse detection algorithm may be different than in the pacer/manual defib/AED mode, as now one may assume that chest compressions are no longer delivered so the algorithm need not be specifically designed to handle chest compressions. That is, in the monitor mode, a "standard motion robust" PR and SpO2 algorithm can be used.

In one embodiment, device 10 has a user input switch 44, such as a knob, to indicate the elected mode setting of device 10. User interface 24 can show the position of the knob or otherwise indicate the operating mode of the monitor-defibrillator. In other embodiments, the user input switch 44 can be a software-based button on a touch-screen user interface, such as on interface 22.

Pulse oximetry module 14 receives one or more PPG signals of a patient from SpO2/PPG sensor 18 and generates a PPG waveform to determine whether a pulse is present. If a pulse is detected but the associated pulse rate is below a predetermined threshold, the signal processing unit assumes that no pulse is present and there is no ROSC. PPG-based pulse detection can be carried out using pulse oximetry hardware and sensors commonly used in clinical practice. The PPG signals for pulse detection and SpO2 measurement can be collected by the same pulse oximetry module and sensor. However, optimal settings of the pulse oximetry hardware are different for PR only measurements than for PR and SpO2 measurements. The pulse oximeter module can be a stand-alone device or may be incorporated as a module or built-in portion of a multiparameter patient monitoring system. Typically, the pulse oximeter provides numerical information of the oxygen saturation of the patient, numerical information of pulse rate, an audible indicator or a "beep" generated at each pulse and a filtered PPG signal waveform.

Figure 3:
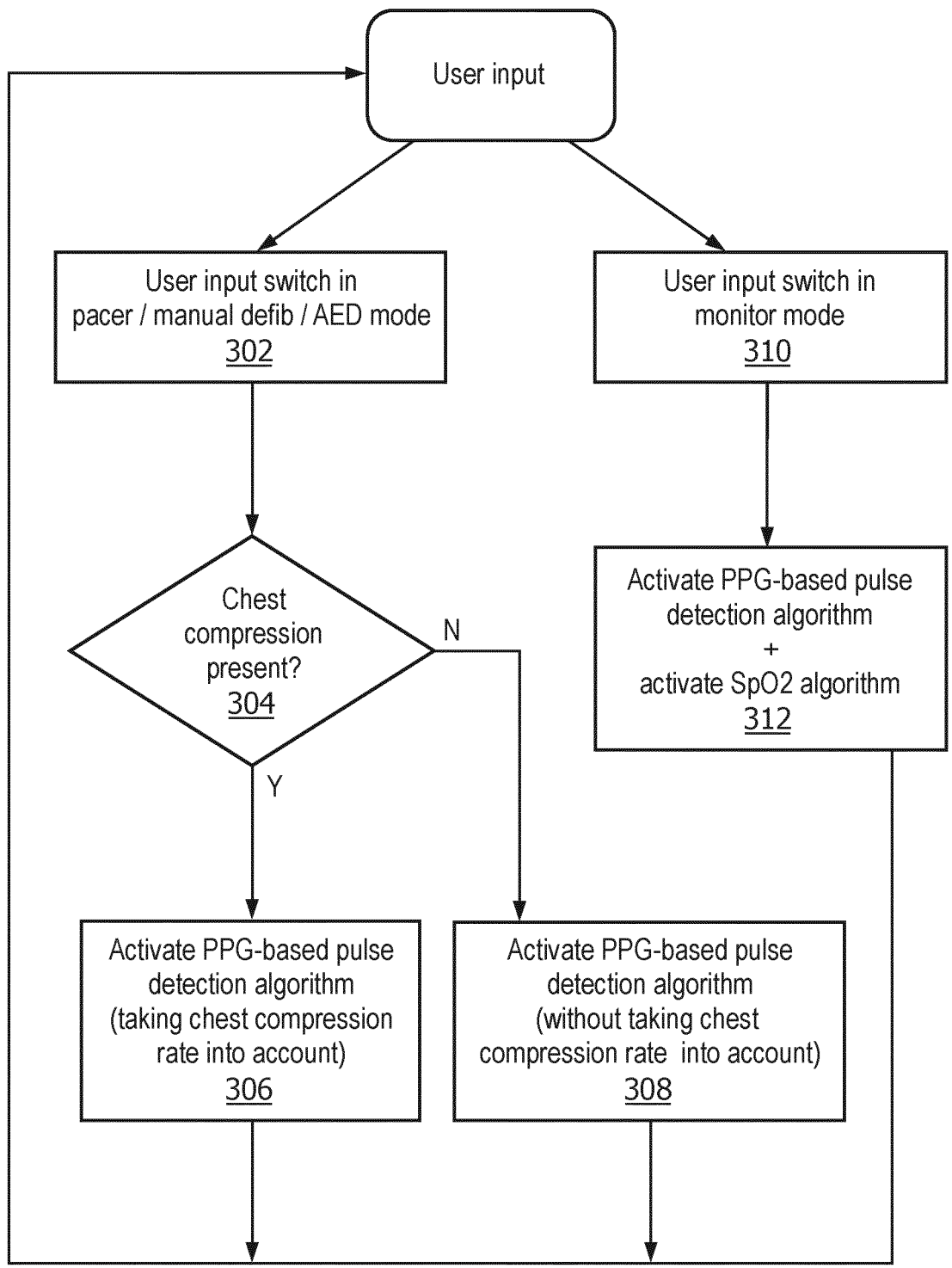
FIG. 3 is a flowchart illustrating operation of a system according to the first embodiment.

FIG. 3 is a simplified flowchart illustrating a method of operation of system 100 executed according to the first embodiment. The operation of the algorithm depends on the mode selection of user input switch 44. If user input switch 44 indicates "pacer/manual defib/AED mode" (302), only the PPG-based pulse detection is run. After the CPR procedure is started, compression detection module 14 determines whether a chest compression is present or not based on a signal received from compression sensor 16 (304). If a chest compression is present, the PPG-based pulse detection algorithm is activated in a mode that takes into account the chest compression rate (306). If a chest compression is not present, the PPG-based pulse detection algorithm is activated in a mode that does not take into account the chest compression rate (308). The process can be repeated as needed. If the user input switch 44 indicates "monitor mode", it is assumed that no chest compressions are being delivered when the user sets the device in this mode (310). In this mode, the PPG-based pulse detection and the SpO2 measurement are run simultaneously (312). Operation of system 100 may be affected by input of other physiological sensors.

Figure 4:
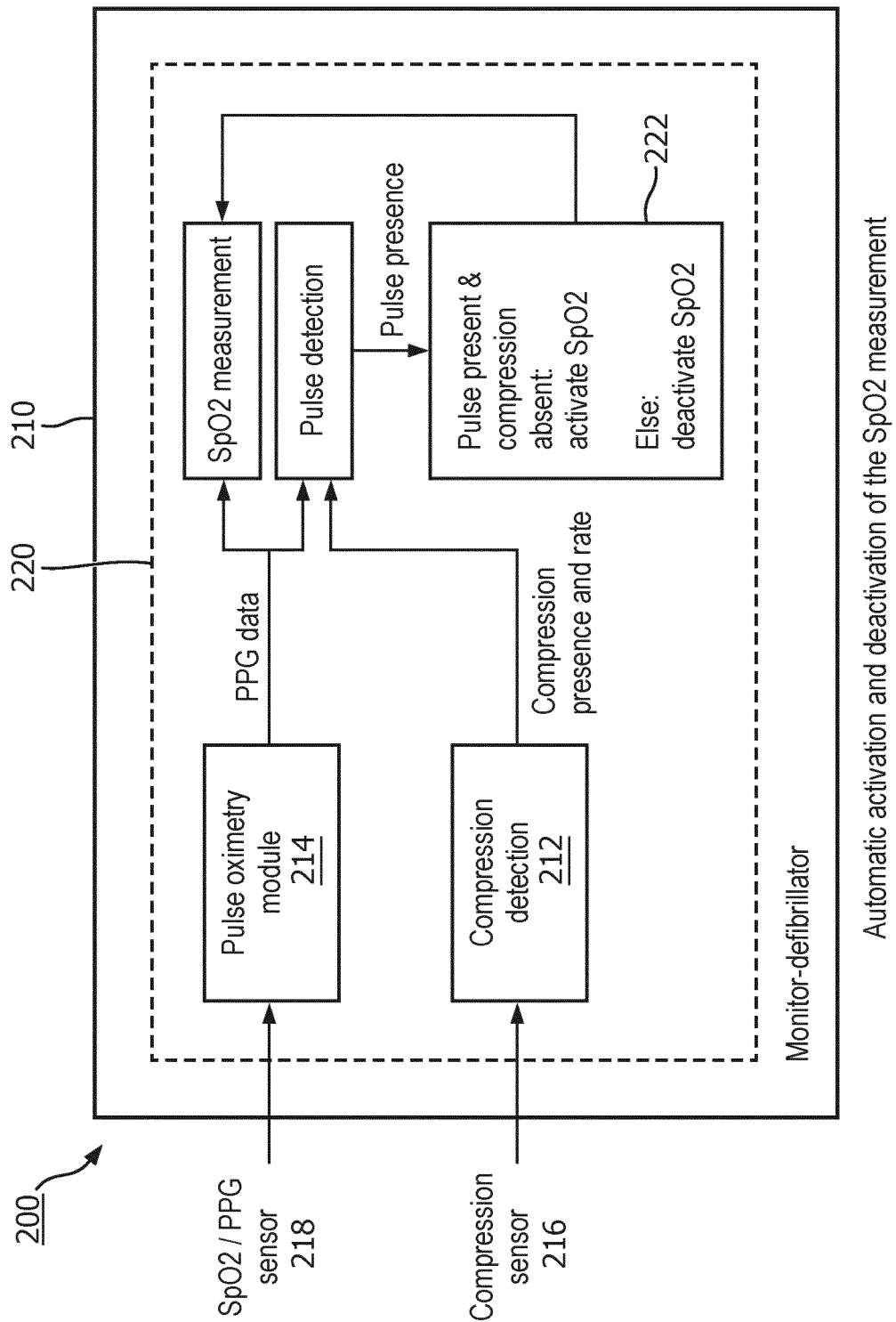
FIG. 4 is a schematic diagram of a second embodiment of a system according to the inventive subject matter having an automatic mode to activate the SpO2 algorithm.

A second embodiment is described with reference to FIGS. 4 and 5. In this embodiment, the SpO2 measurement can be automatically activated and deactivated in any operating mode of the device by using the output of the pulse detection algorithm and the output of the compression detection algorithm. System 200 includes device 210, an SpO2/PPG sensor 218 providing a PPG signal to pulse oximetry module 214, and a compression sensor 216 providing a compression signal to compression detection module 212. Device 210 further includes a status determination unit 222 allowing for the SpO2 measurement to be automatically activated once the pulse detection algorithm detects presence of a spontaneous pulse and the compression detection algorithm detects absence of compression.

When the CPR procedure starts, and device 210 is switched on, signal processing unit 220 activates both the PPG-based CPR pulse-detection algorithm and the SpO2 algorithm. This is independent of the selected mode of device 210. When chest compressions start on the patient, as detected from the analysis of the compression signal, the SpO2 algorithm is deactivated. During chest compressions, SpO2 measurements will become unreliable due to the chest compression artifacts, but the pulse detection algorithm remains active. When loss of a spontaneous pulse has been detected by the pulse detection algorithm during periods without compressions, the SpO2 algorithm is deactivated as a cardiac pulse is required to measure SpO2. When compressions have not occurred during a predetermined time period, for example 10 seconds, and a pulse has been detected, the SpO2 algorithm is activated. Now, a cardiac pulse is present which is required to measure SpO2 and no compression artifacts are present which could have corrupted the SpO2 measurement.

Furthermore, when a pulse has returned it may be clinically desirable to know the patient's oxygen saturation levels to further monitor the patient's status and tailor the therapy. At this point in time a buffer of red and infrared PPG data is available which indicate a cardiac pulse and no compressions. Upon activation of the SpO2 measurement, the algorithm analyzes the buffer of data to directly provide an SpO2 value. This requires that both the red and infrared light emitting diodes are kept on during the mode of pulse detection only.

Thus, activation of the SpO2 algorithm is automatically determined from the output of the pulse detection algorithm and the output of the compression detection algorithm. The PPG-based pulse detection algorithm is tailored to detecting pulse presence and reporting a PR if the heart is beating sufficiently stable to report a PR.

Figure 5:
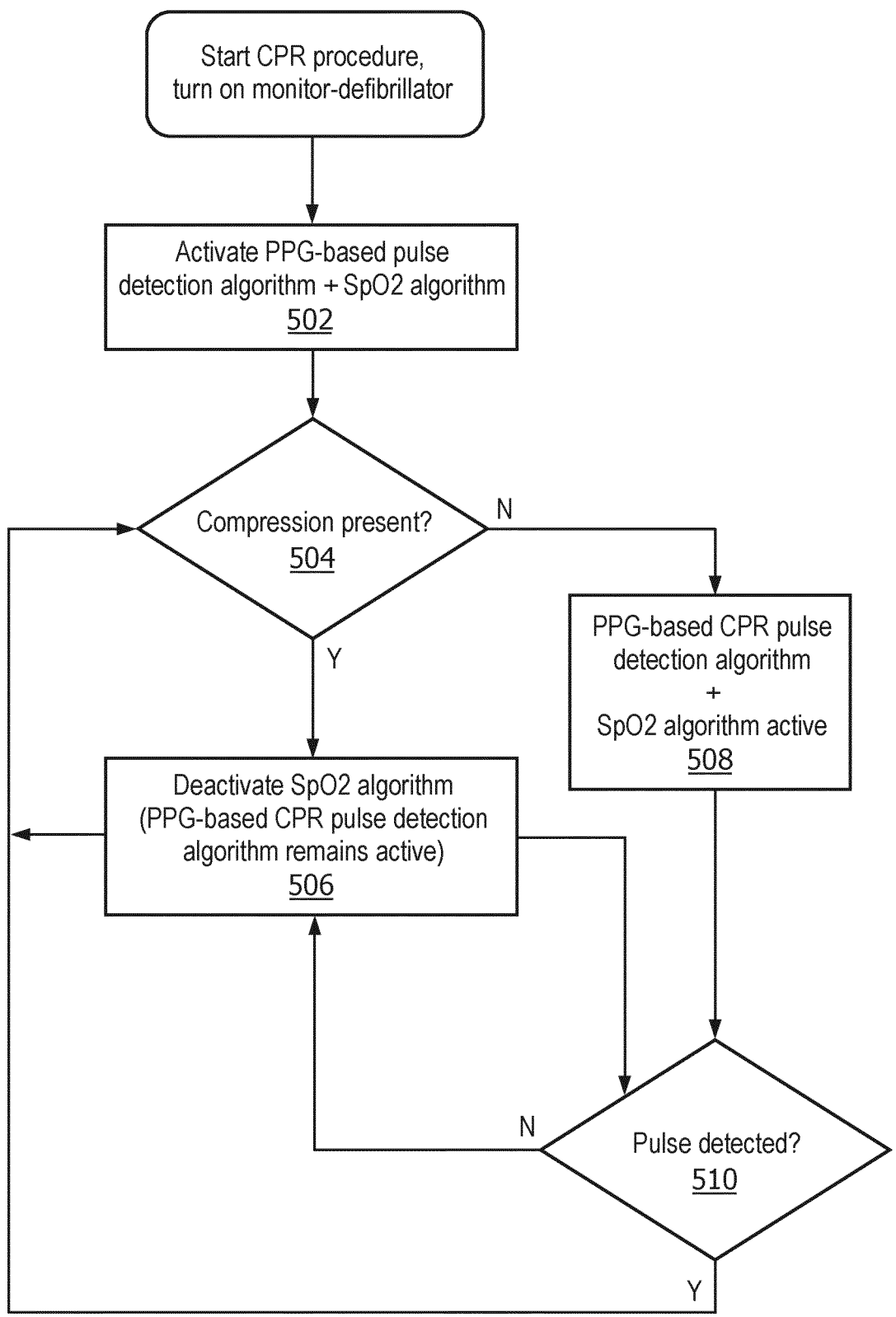
FIG. 5 is a flowchart illustrating the operation of a system according to the second embodiment.

FIG. 5 illustrates operation of system 200. When the device is turned on, both the PPG-based pulse detection algorithm and the SpO2 algorithm are activated (502). The presence of a chest compression is determined (504). If a chest compression is present, the SpO2 algorithm is deactivated, and the PPG-based pulse detection algorithm remains active (506). If a chest compression is not present, both the PPG-based pulse detection algorithm and the SpO2 algorithm remain active (508). The presence of a pulse is verified (510). When there is no pulse detected, the SpO2 algorithm is deactivated (506). If a pulse is present, and a chest compression is present, the PPG-based pulse detection algorithm is activated and the SpO2 algorithm is deactivated (506). The process can be repeated until ROSC is achieved.

According to a third embodiment, the system allows for automatic configuration of the pulse oximetry hardware. Since the PPG signals for PR and SpO2 measurements are collected by the same pulse oximetry module and sensor, the optimal configuration of the pulse oximetry hardware can be adjusted depending on whether PR only or PR and SpO2 measurements need to be performed. This embodiment can be combined with the first or second embodiments described above and/or with a fourth embodiment described below.

Figure 6:
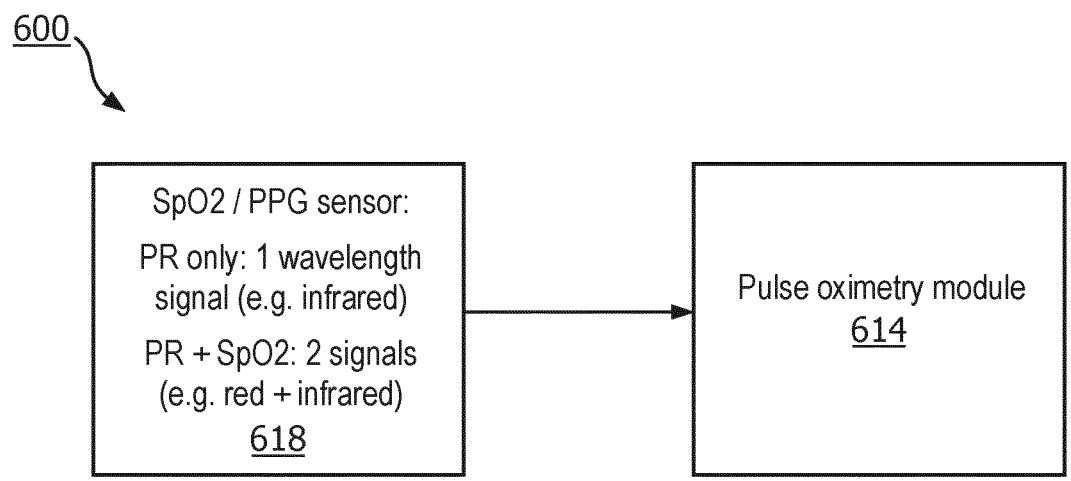
FIG. 6 is a schematic diagram of pulse oximetry hardware and sensor according to a third embodiment of the inventive subject matter.

FIG. 6 illustrates a simplified component 600 of a system and device according to the third embodiment wherein the pulse oximetry module 614 has different optimal configurations for detecting PR only and for providing both PR detection and SpO2 measurement. When a measurement of the PPG signals is used for pulse rate detection only, an SpO2/PPG sensor 618 can provide a measurement at one wavelength. When a measurement of PPG signals is used for pulse rate detection and SpO2 measurement, SpO2/PPG sensor 618 can provide a measurement at two wavelengths. For example, one light emitting diode can be switched off during the PR detection only mode or the light intensity can be increased in the PR detection only mode. Additionally, the algorithm that prevents saturation can be different for PR only mode.

When detecting PR only, only one wavelength may be relevant, for example only infrared is used, and the hardware settings can be optimized to have a maximum signal-to-noise-ratio (SNR) in the infrared PPG signal. For example, the infrared signal level on the analog digital converter (ADC) can be maximized in this setting. The other PPG signal, for example red, may be completely deactivated in this setting at the expense of an additional delay of the SpO2 measurement once this is required. Alternatively, the other PPG signal may be kept on in this setting to have a rapid SpO2 measurement available once this is required.

Furthermore, in this situation the algorithm that prevents saturation of the ADC can have a more aggressive setting. During CPR, motion artifacts can be very large and probe-skin motion is more likely to occur which can have significant effects on the signal level on the ADC, i.e., saturation of the ADC input is more likely to occur. Detection of saturation can be achieved using a low-pass filtered signal. During CPR, the bandwidth of this filter can be set wider than during non-CPR. Alternatively, the allowed margin of the low-pass filtered signal to the maximum input of the ADC can be set larger during CPR than during non-CPR to prevent saturation.

When both PR and SpO2 need to be measured, two PPG signals will be measured, for example red and infrared, and the hardware settings are optimized to have good SNR in both PPG signals and have the signals balanced, i.e., with comparable average level on the ADC.

According to a fourth embodiment, the system allows automatic configuration of the device and related hardware to provide optimal pulse detection. The optimal configuration of the pulse detection algorithm depends on whether chest compressions are being delivered manually or by an automated device. Analysis of the chest compression signal indicates whether chest compressions are being delivered manually or by an automated device and the pulse detection algorithm parameters are adjusted accordingly to assure optimal performance. The PPG-based pulse detection algorithm has different optimal parameter settings for manual and automated chest compression delivery. Parameter settings of the pulse detection algorithm can be adjusted based on analysis of measured compression signals and a compression reference signal. Alternatively, parameter settings of the pulse detection algorithm can be adjusted based on communication between system 100 and the automatic chest compression delivery system or between system 200 and the automatic chest compression delivery system. Communication between system 100 and the automatic chest compression delivery system or between system 200 and the automatic chest compression delivery system can occur via wired or wireless means.

The optimal settings for the pulse detection algorithm are automatically determined by the monitor-defibrillator device, for example by analysis of the impedance signal or another compression reference signal. A compression reference signal can be any of pad impedance, compression depth, compression velocity, compression acceleration or compression force. The analysis of the compression signal can, for example, be determined by the standard deviation of the compression rate, which is expected to be smaller for automated compressions than for manual compressions. An algorithm parameter which depends on the compression method is for instance the predefined bandwidth around the compression rate and its harmonics which is excluded for finding pulse rates. This bandwidth can be, for example [−5 BPM, +5 BPM] for automated compressions, and, for example [−10 BPM, +10 BPM] for manual compressions. In this embodiment, optimal pulse detection can be automatically configured without any user intervention. This embodiment can be combined with any of the embodiments described above.

The inventive subject matter further contemplates a method to control activation of SpO2 measurements in a CPR procedure. Compression presence data and compression rate data can be obtained from a compression sensor, and PPG data are obtained from a pulse oximetry sensor. The compression presence data and compression rate data are processed with a compression detection algorithm to determine whether a chest compression is present. A PPG-based pulse detection algorithm is performed only when compressions are present. Both the PPG-based pulse detection algorithm and an SpO2 measurement algorithm are performed when a spontaneous pulse has been detected and compressions are not detected during a predetermined time period.

Different types of algorithms for PPG-based pulse detection can run during absence of compressions and during presence of compressions.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Applicant(s) reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A device to control activation of oxygen saturation (SpO2) measurements in a cardio-pulmonary resuscitation procedure, comprising:
    a compression detection module for receiving a compression signal and providing compression presence data and compression rate data;
    a pulse oximetry module for receiving one or more photoplethysmography (PPG) signals and providing PPG data;
    a signal processing unit for carrying out a compression detection algorithm based on the received compression presence data and compression rate data; a PPG-based pulse detection algorithm based on the received compression presence data, compression rate data, and the PPG data; and an SpO2 measurement algorithm based on the received compression presence data, compression rate data and the PPG data;
    wherein the SpO2 measurement algorithm is deactivated when compressions are present; and
    wherein the SpO2 measurement algorithm is activated when a spontaneous pulse has been detected and compressions are not detected during a predetermined time period.

2. The device of claim 1, wherein activation of the SpO2 measurement algorithm is determined by a mode-selection of a user input switch of the device.

3. The device of claim 2, wherein the user input switch is a software-based button on a touch-screen user interface.

4. The device of claim 1, wherein activation of the SpO2 algorithm is automatically determined from an output of the PPG-based pulse detection algorithm and an output of the compression detection algorithm.

5. The device of claim 1, wherein the PPG-based pulse detection algorithm and the SpO2 measurement algorithm are both activated when the device is switched on; wherein the signal processing unit monitors both of an output of the PPG-based pulse detection algorithm and an output of the compression detection algorithm; wherein the SpO2 measurement algorithm is subsequently deactivated if either the output of the compression detection algorithm indicates that compressions are present or the output of the PPG-based pulse detection algorithm indicates loss of a spontaneous pulse; and wherein the SpO2 measurement algorithm is subsequently re-activated if the output of the PPG-based pulse detection algorithm indicates that a spontaneous pulse has been detected and if the output of the compression detection algorithm indicates that compressions are not detected during a predetermined time period.

6. The device of claim 1, wherein the one or more PPG signals for pulse detection and SpO2 measurement are collected by the same pulse oximetry module.

7. The device of claim 6, wherein the pulse oximetry module is adapted to allow for optimal configuration depending on whether the one or more PPG signals are used for pulse rate detection only or for pulse rate detection and SpO2 measurement.

8. The device of claim 6, wherein a measurement of the one or more PPG signals used for pulse rate detection only is based on a measurement at one wavelength, and wherein a measurement of PPG signals used for pulse rate detection and SpO2 measurement is based on a measurement at two wavelengths.

9. The device of claim 1, wherein a parameter of the PPG-based pulse detection algorithm is automatically adjusted depending on whether chest compressions are delivered manually or by an automated device.

10. The device of claim 9, wherein the PPG-based pulse detection algorithm has different optimal parameter settings for manual chest compression and for automated chest compression, and wherein parameter settings of the PPG-based pulse detection algorithm are adjusted based on analysis of measured compression signals and a compression reference signal.

11. The device of claim 1, wherein the compression detection module is adapted to determine the compression reference signal based on pad impedance, compression depth, compression velocity, compression acceleration or compression force.

12. A system to control activation of oxygen saturation (SpO2) measurements in a cardio-pulmonary resuscitation procedure, the system comprising:
    a compression sensor configured to provide a chest compression signal;
    a pulse oximetry sensor configured to provide one or more photoplethysmography (PPG) signals; and
    the device as claimed in claim 1 arranged to receive the chest compression signal and the one or more PPG signals, and wherein the device is configured to determine whether a chest compression is delivered manually or automatically, and wherein parameter selections for the compression detection algorithm, the PPG-based pulse detection algorithm, and the SpO2 measurement algorithm are adjusted accordingly.

13. The system of claim 12, wherein the one or more PPG signals for pulse detection and SpO2 measurement are collected by the same pulse oximetry module and pulse oximetry sensor.

14. The system of claim 13, wherein the configuration of the pulse oximetry module and pulse oximetry sensor are adapted to measure different PPG signals depending on whether the PPG signals are used for pulse rate detection only or for pulse rate detection and SpO2 measurement.

15. A method to control activation of oxygen saturation (SpO2) measurements in a cardio-pulmonary resuscitation procedure, the method comprising:
- obtaining compression presence data and compression rate data from a compression sensor;
- obtaining photoplethysmography (PPG) data from a pulse oximetry sensor;
- processing the compression presence data and compression rate data with a compression detection algorithm, by a signal processing unit, to determine whether a chest compression is present;
- deactivating $SpO_2$ measurement algorithm when compressions are present using the signal processing unit; and
- activating both the PPG-based pulse detection algorithm and an SpO2 measurement algorithm when a spontaneous pulse has been detected and compressions are not detected during a predetermined time period using the signal processing unit.

\* \* \* \* \*